(12) United States Patent
Liu et al.

(10) Patent No.: US 6,190,916 B1
(45) Date of Patent: Feb. 20, 2001

(54) TROPONIN I COMPOSITION

(75) Inventors: Shigui Liu; Min Yuan Zhang, both of Toronto; Qinwei Shi, Etobicoke, all of (CA)

(73) Assignee: Spectral Diagnostics, Inc., Toronto (CA)

( * ) Notice: Under 35 U.S.C. 154(b), the term of this patent shall be extended for 0 days.

(21) Appl. No.: 09/342,578

(22) Filed: Jun. 29, 1999

(51) Int. Cl.$^7$ ................ G01N 31/00; G01N 33/557; C12N 9/50; C07K 1/00; C07K 14/00

(52) U.S. Cl. .............. 436/17; 435/7.1; 435/7.6; 435/183; 435/184; 435/219; 435/7.94; 435/13; 435/69.3; 435/967; 435/972; 436/8; 436/15; 436/17; 436/517; 436/518; 436/536; 436/811; 424/569; 530/350; 530/412; 530/414; 530/417; 530/402; 530/403; 530/391.5; 530/391.7; 530/807; 530/814

(58) Field of Search ................ 435/7.1, 7.6, 183, 435/184, 219, 7.94, 13, 69.3, 967, 972; 436/8, 17, 15, 517, 518, 536, 811; 424/569; 530/350, 412, 414, 417, 402, 403, 391.5, 391.7, 807, 814

(56) References Cited

U.S. PATENT DOCUMENTS

| | | | |
|---|---|---|---|
| 5,583,200 | * 12/1996 | Larue et al. | 530/350 |
| 5,795,725 | * 8/1998 | Buechler et al. | 435/7.1 |
| 5,834,210 | * 12/1998 | Liu et al. | 435/7.1 |
| 5,834,220 | * 11/1998 | Wicks et al. | 435/7.92 |
| 5,846,738 | * 12/1998 | Seidel et al. | 435/7.1 |
| 5,851,554 | * 12/1998 | Lee et al. | 424/569 |
| 5,925,533 | * 6/1999 | Doth et al. | 435/7.94 |

OTHER PUBLICATIONS

Chang et al., 1997, Arch Pathol Lab Med 122:320.
Henderson et al., 1998, Clinica Chimica Acta 272:93–100.
Lum, 1979, Clinical Chemistry 25:873–76.
Mair et al., 1995, Clin. Chem. 41:1266–72.
Makioka et al., 1979, J. Biochem. 85:967–75.
Artuso et al., 1998, Clinical Chem. 44(6):A118, Suppl. Abs 511.
Hall et al., 1998, Clinical Chem. 43(6):A128, Abs 100.
Bhayana et al., 1998, Clinical Chem. 43(6):A128, Abs 101.
Ooi et al., 1998, Clinical Chem. 43(6):A128, Abs 103.
Sintar et al., 1998, Clinical Chem. 43(6):A118, Abs 665.
CAP Today, 1998, Advertisement: Circle No. 10, Cardiolmmune.
Artuso et al., 1998, Characterization of a New Liquid Stable Control for Troponin I, CKMB, and Myoglobin.

* cited by examiner

*Primary Examiner*—Long V. Le
*Assistant Examiner*—Gailene R. Gabel
(74) *Attorney, Agent, or Firm*—Klauber & Jackson

(57) ABSTRACT

The present invention relates to stable compositions useful as primary standards and calibrators and controls comprising a cardiac troponin I (cTnI) such as native, recombinant, addition and deletion forms thereof, whether or not complexed with other troponin subunits such as TnC and/or TnT, in an inactivated human serum. The compositions are obtained by incubating troponin complexes with human serum. The compositions are characterized by an immunodetectability ratio of epitopes on the N-terminal segment to epitopes on the C-terminal segment substantially equivalent to that of pooled, fresh serum from acute myocardial infarction patients.

18 Claims, No Drawings

TROPONIN I COMPOSITION

FIELD OF THE INVENTION

The present invention relates to stable compositions useful as primary standards and calibrators and controls comprising a cardiac troponin I (cTnI) such as native, recombinant, addition and deletion forms thereof, whether or not complexed with other troponin subunits such as TnC and/or TnT, in an inactivated human serum. The compositions are obtained by incubating troponin I or troponin I complexes with human serum. The compositions are characterized by an immunodetectability ratio of epitopes on the N-terminal segment to epitopes on the C-terminal segment substantially equivalent to that of cardiac troponin I in pooled, fresh serum from patients having undergone an acute myocardial infarction.

BACKGROUND OF THE INVENTION

Early and accurate assessment of suspected acute myocardial infarction is critically dependent on the sensitive and specific detection of intracellular cardiac muscle components released into the circulation, in order to distinguish a potentially lethal event in need of emergency measures from non-life threatening conditions such as angina and non-cardiac chest pain such as dyspepsia. Early electrocardiographic changes are neither adequately specific nor sensitive, and the medical profession has come to rely on serum biochemical markers of cardiac tissue injury for early diagnosis. Initially, the serum markers creatine kinase (CK) and specifically the cardiac CK-MB isoform were used; subsequently myoglobin as a more sensitive early indicator of cardiac damage became preferred. More recently, the cardiac troponin complex and its cardiac-specific subunits have come to be preferred as markers of myocardial damage because of their high specificity. A combination of these analytes, provides a high degree of diagnostic accuracy. If performed in the emergency room, an early and accurate diagnosis of myocardial damage significantly enhances the safe recovery of a suspected heart attack victim.

Troponin is a generic term used to identify a muscle protein integrally involved in the calcium-dependent regulation of muscle contraction. Troponin exists in both cardiac and skeletal muscle as a non-covalently-bound complex of three subunits; the isoforms troponin C, the calcium-binding subunit; troponin I, the inhibitory subunit; and troponin T, which locates the troponin complex on tropomyosin. Differences exist between the amino acid sequences of the cardiac muscle and skeletal muscle troponin isoforms, and these differences are exploited in diagnostic tests which specifically measure the cardiac isoforms of the troponin to assist the diagnostician in determining if a cardiac event has taken place.

cTnI is a low molecular weight protein containing about 210 amino acid residues. When a cardiac event such as myocardial infarction occurs, cTnI together with cTnC and cTnT are released into the blood stream as a result of deterioration of cardiac muscle. cTnI and cTnT isoforms are specific to cardiac tissue and detectably distinguishable from skeletal isoforms.

It has been suggested that serum troponin may exist as complexes usually referred to as CIT, IT, CI and CT complexes. Troponin subunits, especially cTnI, undergo various degradation reactions resulting in the formation of complexes that differ in molecular weight, tertiary structure and other physical and chemical characteristics. One of these characteristics is that epitopes which may originally have been exposed for reaction with selected antibodies are no longer so exposed and may even have been destroyed. See for example:

Bodor et al., Clin. Chem. 38(11), 2203 (1992)
Adams et al., Clin. Chem. 40(7), 1291 (1994)
Adams et al., Circulation 88(1), 101 (1993)
Adams et al., New England Journal of Medicine 330(10), 670 (1994)

A number of instruments have been designed and are commercially available to measure total cTnI in the blood of suspected heart attack victims. These include the Abbott AxSYM, the Dade OPUS, the Bayer IMMUNO-1, the Beckman ACCESS, and the Dade STRATUS. Each of these instruments measure cTnI be reacting different epitopes with different antibodies. One, for example, measures an epitope near the C-terminus of the molecule whereas another measures an epitope near the middle of the molecule or a the N-terminus.

The epitope measured or the antibodies employed do not detract from the accuracy of the instrument or its sensitivity. However, it does mean that each instrument has a different reference range and each has a different value indicative of a positive reading. For example, on the Dade STRATUS a positive test is recognized by a value of >1.5 ng/mi. On the ACCESS device, it is >0.2 and on AxSYM it is >2.0. These variations sometimes cause confusion if a patient is moved from one hospital to another or the technician is working on different instruments.

Other problems with utilizing cTnl as an indication of cardiac damage is the rapid degradation of the molecules and the fact that its concentration varies among different patients. The problems can be alleviated by utilizing fresh samples. However, these are difficult to obtain because patients present at different times after the onset of chest pain and the variation amongst patients is never known with any degree of confidence.

The art has sought to deal with the problems by utilizing pooled patients' serum to calibrate the various instruments. The solution has been unsatisfactory because the pooled sample degrades during storage even at low temperatures.

The art has long searched for some method of standardization so that the reference ranges on the different instruments would be the same. The invention described and claimed herein makes such standardization possible. For convenience, the term cTnI will be used in the Specification and Claims to refer to natural cTnI, as well as addition and deletion analogs thereof whether isolated from a natural source or produced by recombinant techniques. It will include also complexes of natural cTnI and such analogs with the other troponin isoforms, cTnC and cTnT. It will refer also to those analogs of natural cTnI which have been extended at either end by the addition of other amidno acid segments. The criteria for recognizing a troponin useful in this invention is that it will act like natural ctnl to achieve the novel, stable compositions of the invention.

The ratio of immunodetectability is determined by a separate determination of a detectable epitopes in the area of the C-terminus and the area of the N-terminus of the molecule. Although separate determinations are made, they are made on the same sample at the same time. The epitope on the N-segment is measured with the STRATUS device. The epitope on the C-segment is measured with the ACCESS device.

DESCRIPTION OF THE INVENTION

The compositions of this invention when utilized in diagnostic procedures perform in a fashion similar to fresh patient serum samples even after long storage periods. They thus offer prolonged stability and when prepared from recombinant cTnI and fresh serum, better lot-to-lot consistency and unlimited availability.

Various forms of cardiac troponin I may be used in the present invention, including but not limited to native troponin I, recombinant troponin I, synthetic troponin I, and various addition or deletion forms thereof. Synthetic proteins may be made by, for example, solid-phase synthesis. An example of a recombinant form of cardiac troponin I with a 6-amino acid leader sequence is disclosed in U.S. Pat. No. 5,834,210, incorporated herein by reference. Other forms may be used which do not detract from the purposes herein.

The stable standardization compositions of this invention are obtained by mixing a cTnI with human serum at selected concentrations and allowing the mixture to incubate at about 35° C. to about 44° C., preferably 35° C. to 37° C. until the desired equilibrium composition has been obtained. The desired equilibrium composition has an immunodetectability ratio of the N-terminus to the C-term-inus of cTnI substantially equivalent to that of pooled, fresh serum from acute myocardial infarction patients.

Typically the concentration of cTnI will be from about 20 to about 100 ng/ml of serum, preferably 20 to 40 ng/ml, and most preferably about 30 ng/ml. This concentration is based on the determination of the purified cTnI utilizing the known Bradford assay with bovine serum albumin as the standard.

The incubation time is not critical. It may vary from about 3 to about 7 days depending upon the properties of the serum.

Optimum parameters for a specific form of cTnI and a specific serum can be readily determined by removing aliquots of the mixture and determining the immunodetectability ratio. Typically some variations from the above described parameters can be tolerated without unacceptably adverse results.

During the incubation time, the proteinases naturally present in the serum will act upon the mixture to cause the degradation of TnI until the desired ratio of immunodetectability is reached. At that time, the proteinases are substantially inactivated by heating or other means. Neither the temperature or the time is critical so long as they are not injurious to the mixture or its activity. Typically, the inactivation temperature is at least above about 37° C., but higher temperatures can be tolerated to decrease the time necessary for deactivation. The conditions will be from about 37° C. to 60° C., preferably 50° C. to 60° C., for from about 30 to 90 minutes. As indicated, wide variations are possible.

The proteinases may also be inactivated by known chemical means. One especially useful procedure comprises the use of inhibitor cocktails such as mixtures of phenylmethylsulphonylchloride (PMSF), ethylenediamine tetracetic acid, trans-epoxysuccinyl- L-leucylamidino(4-guanidino)butane and pepstatin. The inhibitors may be used at ambient temperature, i.e, around 20° C. to 30° C.

The extent of inactivation need only be that which results in a substantially stable product. Residual proteinase activity that does not affect the quality or utility of the product is tolerated.

Those skilled in the art will recognize that the achievement of stable compositions is not necessarily dependent on these proteinases which are naturally present in blood. The achievement of stable compositions can be accelerated by the addition of selected proteinases, such as native or recombinant proteinases that occur naturally in blood, as well as from other sources. Inactivation of these proteinases may be carried out by the appropriate methods for inactivation known to one of skill in the art.

It will also be recognized that those compositions having an immunodetectability ratio substantially equivalent to that of the pooled, fresh serum from acute myocardial infarction patients when measured on the STRATUS and the ACCESS machines, may manifest a different ratio when measured on other machines. Typically the ratio of the STRATUS and ACCESS values of the desired product is about 7:1. The criteria is that the immunodetectability of the epitope in the area of the N-terminus be appreciably higher than that in the area of the C-terminus. It appears that the rate at which the proteinases degrade the C-terminus region of the cTnI is higher than the rate at which the N-terminus region of the cTnI is degraded. Thus, with the passage of time, the number of N-terminal epitopes in all of the molecules in the mixture becomes higher than the number of C-terminal epitopes.

In fact, it will be apparent that the activity of the proteinases can be terminated at substantially any point in time after the mixture has been formed and the resulting mixture will be stable. It has been observed, however, that after the passage of an appropriate period of time with a majority of patients undergoing or having undergone a cardiac event, the ratio of immunodetectable N-epitopes to C-epitopes based on the STRATUS and ACCESS values is approximately 7:1. Accordingly, in the practice of this invention it is desirable, but not essential to achieve the approximately same ratio. In practice, however, stable compositions in which the ratio is from about 4:1 to about 9:1 can be used in the practice of the invention, 6:1 to 8:1 being preferred. As noted above, the composition is intended to have substantially the same ratio as that of cTnI in patients serum.

It is not practical to isolate a formed stable composition from the blood of patients since there is appreciable variation in the ratio between patients and with the age of the sample. The problems for obtaining efficient and useful standards and calibrators results from this variation. The salient advantage of the novel compositions of this invention is that they are stable for an extended period of time and behave like fresh human serum. It is therefore possible for manufacturers of assay devices such as those mentioned above to use the compositions to develop those devices to validate their assays compared to other devices with confidence and to utilize accurate quality control procedures.

The present invention is also directed to an assay kit for determining the level of troponin I in a patient sample relative to a troponin I standard comprising means for measuring troponin I in said sample; and a troponin I composition of claim 1. Means for detecting troponin I may take the form of any of the various assay kits for troponin I such as those described herein. By use of the troponin I standard of the present invention in such assays, the levels of troponin I in patient samples may be standardized, improving the diagnostic utility of the analyte as well as permitting the establishment of normal and abnormal ranges both within and across laboratories.

The following examples are given by way of illustration only.

EXAMPLE 1

PREPARATION OF A SERUM-PROCESSED TROPONIN I STANDARD

A stable troponin I standard was prepared in accordance with the present invention by incubating under sterile conditions 30 ng/ml of recombinant troponin I consisting of a noncovalent complex of recombinant troponin C and a modified recombinant human cardiac troponin I expressed with a 6 amino acid leader sequence at the N-terminus (as described in U.S. Pat. No. 5,834,210). At the times indicated in Table 1, below, samples were taken for analysis in the STRATUS and ACCESS troponin I immunoassays. As noted above, the STRATUS assay uses two monoclonal antibodies which recognize the N-terminal portion of the troponin I molecule; the ACCESS assay uses two monoclonal antibodies which recognize the C-terminal portion of the troponin I molecule. During proteolytic degradation, loss of C-terminal detection results in an increase in the ratio of the STRATUS to the ACCESS ("S/A") assay results.

TABLE 1

Immunodetectability (in ng/ml) of troponin I after incubation in human serum

| Time(hrs): | 0 | 4 | 7 | 16 | 24 | 48 | 72 | 144 |
|---|---|---|---|---|---|---|---|---|
| 30 ng/ml troponin I-troponin C complex* | | | | | | | | |
| STRATUS (S) | 11.85 | 23.85 | 26.70 | 27.50 | 35.13 | 28.25 | 26.15 | 21.55 |
| ACCESS (A) | 15.84 | 15.65 | 13.48 | 12.94 | 15.65 | 8.1 | 6.49 | 3.54 |
| S/A | 0.75 | 1.52 | 1.98 | 2.13 | 2.24 | 3.49 | 4.03 | 6.09 |
| 30 ng/ml of troponin C-troponin I-troponin T complex* | | | | | | | | |
| STRATUS (S) | 19.10 | 29.95 | 35.95 | 34.75 | 35.45 | 36.05 | 33.70 | 25.85 |
| ACCESS (A) | 24.14 | 24.86 | 21.53 | 19.73 | 15.14 | 12.76 | 9.99 | 5.06 |
| S/A | 0.79 | 1.20 | 1.67 | 1.76 | 2.34 | 2.83 | 3.37 | 5.11 |

*Determined by Bradford assay before complex formation.

As shown in Table 1 above for both a complex of troponin I and troponin C, as well as a complex of troponin C, I and T, during incubation with serum, the C-terminus of troponin I degrades, as shown by the decreasing values in the ACCESS assay, in contrast to the relative stability of the N-terminus as shown by the values in the STRATUS assay.

Example 2

Stability of the Troponin I Composition

The stability of the troponin I compositions of the present invention was evaluated by storage at −20 C, followed by assay in both the STRATUS and ACCESS troponin I assays. Four concentrations of troponin I were used at the levels shown in the Tables. The results using a troponin I-troponin C complex are shown in Table 2, and the results with a troponin C-I-T complex in Table 3.

TABLE 2

Stability of troponin I-troponin C

| | Stratus | | | | Access | | |
|---|---|---|---|---|---|---|---|
| Level | day 0 | day 10 | day 121 | Level | day 0 | day 10 | day 121 |
| 1 | 0.75 | 0.65 | 0.90 | 1 | 0.123 | 0.141 | 0.187 |
| 2 | 1.60 | 1.40 | 1.70 | 2 | 0.243 | 0.240 | 0.341 |
| 3 | 3.25 | 3.05 | 3.40 | 3 | 0.451 | 0.468 | 0.631 |
| 4 | 6.35 | 6.25 | 6.30 | 4 | 0.992 | 0.827 | 1.180 |

TABLE 3

Stability of troponin I-troponin C-troponin T

| | Stratus | | | | Access | | |
|---|---|---|---|---|---|---|---|
| Level | day 0 | day 10 | day 121 | Level | day 0 | day 10 | day 121 |
| 1 | 0.70 | 0.60 | 0.60 | 1 | 0.120 | 0.127 | 0.158 |
| 2 | 1.65 | 1.40 | 1.80 | 2 | 0.222 | 0.241 | 0.372 |

TABLE 3-continued

Stability of troponin I-troponin C-troponin T

| | Stratus | | | | Access | | |
|---|---|---|---|---|---|---|---|
| Level | day 0 | day 10 | day 121 | Level | day 0 | day 10 | day 121 |
| 3 | 2.95 | 2.55 | 3.10 | 3 | 0.433 | 0.473 | 0.688 |
| 4 | 6.20 | 5.35 | 5.90 | 4 | 0.875 | 0.826 | 1.102 |

The results clearly show the storage stability of the compositions of the invention.

Example 3

Immunodetectability compared to pooled patient serum

The equivalence or similarity between the TnI composition of the present invention and that of pooled fresh acute myocardial infarction (AMI) patient serum was evaluated by STRATUS, ACCESS, OPUS and CARDIAC STATUS kits. Two lots of the TnI composition of the invention and two lots of the TnI composition of the pooled, fresh AMI patient serum, both in four concentrations, were compared in terms of immunodetectability by the above mentioned TnI assays. The results are shown in the following Table 4.

TABLE 4

I. Troponin I composition of the present invention

| Lot #1 | Level | Stratus (ng/ml) | Access (ng/ml) | S/A* | STATus (qualitative) | Opus (ng/ml) |
|---|---|---|---|---|---|---|
| | 1 | 0.80 | 0.152 | 5.26 | Negative | 1.29 |
| | 2 | 1.50 | 0.266 | 5.64 | Trace | 2.51 |
| | 3 | 3.10 | 0.501 | 6.19 | Positive | 5.39 |
| | 4 | 6.00 | 1.068 | 5.62 | Positive | 9.82 |

Ave: 5.68

| Lot #2 | Level | Stratus (ng/ml) | Access (ng/ml) | S/A* | STATus (qualitative) | Opus (ng/ml) |
|---|---|---|---|---|---|---|
| | 1 | 0.80 | 0.096 | 8.33 | Negative | 1.12 |
| | 2 | 1.60 | 0.262 | 6.11 | Trace | 2.46 |
| | 3 | 3.20 | 0.553 | 5.79 | Positive | 5.09 |
| | 4 | 6.50 | 0.871 | 7.46 | Positive | 11.10 |

Ave: 6.92

II. TnI calibrator derived from freshly pooled AMI patient serum

| Lot #1 | Level | Stratus (ng/ml) | Access (ng/ml) | S/A | STATus (qualitative) | Opus (ng/ml) |
|---|---|---|---|---|---|---|
| | 1 | 0.85 | 0.099 | 8.59 | Negative | n/a |
| | 2 | 1.80 | 0.257 | 7.00 | Trace | n/a |
| | 3 | 3.15 | 0.414 | 7.61 | Positive | n/a |
| | 4 | 6.80 | 0.995 | 6.83 | Positive | n/a |

Ave:7.51

| Lot #2 | Level | Stratus (ng/ml) | Access (ng/ml) | S/A* | STATus (qualitative) | Opus (ng/ml) |
|---|---|---|---|---|---|---|
| | 1 | n/a | n/a | n/a | n/a | |
| | 2 | 7.20 | 0.856 | 8.41 | Positive | 11.36 |
| | 3 | 10.65 | 1.220 | 8.73 | Positive | 18.85 |
| | 4 | 26.75 | 3.730 | 7.17 | Positive | 54.10 |

Ave: 8.10

*S/A: ratio of Stratus value over Access value.

While the invention has been described and illustrated herein by references to the specific embodiments, various specific material, procedures and examples, it is understood that the invention is not restricted to the particular material, combinations of material, and procedures selected for that purpose. Indeed, various modifications of the invention in addition to those described herein will become apparent to those skilled in the art from the foregoing description and the accompanying figures. Such modifications are intended to fall within the scope of the appended claims.

Various publications are cited herein, the disclosures of which are incorporated by reference in their entireties.

What is claimed is:

1. A substantially stable composition for use as a cardiac troponin I standard comprising a proteolytically-degraded cardiac troponin I in proteinase-inactivated human serum, wherein an immunodetectability ratio of N-terminal epitopes to C-terminal epitopes of said proteolytically-degraded cardiac troponin I is substantially equivalent to the immunodetectability ratio of N-terminal epitopes to C-terminal epitopes of cardiac troponin I in pooled, fresh serum of acute myocadial infarction patients.

2. The composition of claim 1 wherein said standard comprising proteolytically-degraded cardiac troponin I is derived from a cardiac troponin I selected from the group consisting of a complex of a cardiac troponin I, troponin C and troponin T; a complex of a cardiac troponin I and troponin C; and a cardiac troponin I.

3. The composition of claim 2 wherein said cardiac troponin I is selected from the group consisting of native troponin I, recombinant troponin I, synthetic troponin I, modified troponin I, and combinations thereof.

4. The composition of claim 3 wherein said modified troponin I is an addition or deletion analog thereof.

5. The composition of claim 1 wherein the immunodetectability ratio is determined using at least two antibodies which recognize the N-terminal region of troponin I, and at least two antibodies which recognize the C-terminal region of troponin I.

6. The composition of claim 1 wherein said proteinase-inactivated human serum comprises human serum wherein proteinase activity therein is inactivated to obtain the substantially stable composition.

7. The composition of claim 6 wherein said proteinase activity therein is inactivated by a method selected from the group consisting of addition of protease inhibitors and heat inactivation of said composition.

8. The composition of claim 1 wherein said cardiac troponin I is recombinant human cardiac troponin I.

9. An assay kit for determining a level of troponin I in a patient sample relative to the cardiac troponin I standard of claim 1 comprising (i) means for measuring troponin I in said sample; and (ii) said troponin I composition.

10. A method for preparing a substantially stable proteolytically-degraded cardiac troponin I composition comprising sequential steps of (a) adding a cardiac troponin I into human serum;

(b) incubating the serum containing the cardiac troponin I for a period of time to undergo proteolytic degradation by proteinases to achieve an immunodetectability ratio of N-terminal epitopes to C-terminal epitopes substantially equivalent to the immunodetectability ratio of cardiac troponin I in pooled, fresh serum of acute myocardial infarction patients; and (c) inactivating said proteinases in said serum.

11. The method of claim 10 wherein said cardiac troponin I is selected from the group consisting of a complex of a cardiac troponin I, troponin C and troponin T; a complex of a cardiac troponin I and troponin C; and a cardiac troponin I.

12. The method of claim 10 wherein said cardiac troponin I is selected from the group consisting of native troponin I, recombinant troponin I, synthetic troponin I, modified troponin I, and combinations thereof.

13. The method of claim 12 wherein said modified troponin I is an addition or deletion analog thereof.

14. The method of claim 10 wherein said cardiac troponin I is recombinant human cardiac troponin I.

15. The method of claim 10 wherein said incubation is performed at from about 35° C. to about 44° C.

16. The method of claim 10 wherein exogenous proteinases are added to said human serum.

17. The method of claim 10 wherein said proteinases in said human serum are inactivated by a method selected from the group consisting of addition of protease inhibitors and heat-inactivation of said proteinases in said cardiac troponin I composition.

18. A method for preparing the cardiac troponin I composition of claim 1 comprising (a) adding a cardiac troponin I into human serum;

(b) incubating the serum containing the cardiac troponin I at a temperature of from about 35° C. to about 44° C. for a period of time to undergo proteolytic degradation by proteinases to achieve said immunodetectability ratio in claim 1;

(c) inactivating said proteinases in said serum.

* * * * *